United States Patent [19]

Schnurr et al.

[11] Patent Number: 5,512,697
[45] Date of Patent: Apr. 30, 1996

[54] PREPARATION OF ALIPHATIC ALPHA, OMEGA-AMINONITRILES

[75] Inventors: Werner Schnurr, Herxheim; Rolf Fischer, Heidelberg; Peter Bassler, Viernheim; Wolfgang Harder, Weinheim, all of Germany

[73] Assignee: BASF Aktiengesellschaft, Ludwigshafen, Germany

[21] Appl. No.: 370,606

[22] Filed: Jan. 10, 1995

[30] Foreign Application Priority Data

Dec. 27, 1994 [DE] Germany ............... 44 46 894.6

[51] Int. Cl.$^6$ ................................. C07C 253/30
[52] U.S. Cl. ................................. 558/459
[58] Field of Search ........................... 558/459

[56] References Cited

U.S. PATENT DOCUMENTS 5,151,543  9/1992  Ziemecki ............... 558/459

FOREIGN PATENT DOCUMENTS

WO/92/21650  12/1992  WIPO.
WO/93/16034   8/1993  WIPO.

*Primary Examiner*—Joseph Paul Brust
*Attorney, Agent, or Firm*—Keil & Weinkauf

[57] ABSTRACT

Aliphatic alpha,omega-aminonitriles are prepared by partial hydrogenation of aliphatic alpha,omega-dinitriles at elevated temperatures and superatmospheric pressure in the presence of a base and of a hydrogenation catalyst, by carrying out the hydrogenation in the presence of ammonia and lithium hydroxide or of a compound which gives lithium hydroxide during the hydrogenation.

3 Claims, No Drawings

PREPARATION OF ALIPHATIC ALPHA, OMEGA-AMINONITRILES

The present invention relates to an improved process for the preparation of aliphatic alpha,omega-aminonitriles by partial hydrogenation of aliphatic alpha,omega-dinitriles at elevated temperatures and superatmospheric pressure in the presence of a base and of a hydrogenation catalyst.

U.S. Pat. No. 5,151,543 describes the partial hydrogenation of aliphatic dinitriles to the corresponding aminonitriles in the presence of Raney nickel catalysts. In this process, the solvent used is either ammonia or an alcohol, an inorganic base additionally being required when alcohol is used. In U.S. Pat. No. 5,151,543, it is expressly stated that no further base is required when ammonia is used as the solvent.

A particular disadvantage in the process according to U.S. Pat. No. 5,151,543 is that, when ammonia is used, the yield is only from 60 to 62%, depending on the conversion, and relatively large amounts of hexamethylenediamine are formed (cf. Example 1).

With the use of methanol as the solvent and sodium hydroxide instead of ammonia, the process of U.S. Pat. No. 5,151,543 gives yields (63%) and conversions comparable with those when ammonia is used (Example 3). With the use of an alcohol and of a hydroxide as the base, the large amounts of solvent in addition to the unsatisfactory yield are disadvantageous since the dinitrile can be used only in an amount of about 10% by weight, whereas about five times the amount (47% by weight) can be employed when ammonia is used. The use of a further assistant (alcohol) is also disadvantageous since this has to be removed completely after the reaction if the aminonitrile prepared is 6-aminocapronitrile, which can be cyclized to caprolactam.

In the process of WO 93/16034, the yield of aminocapronitrile can be increased by hydrogenating adiponitrile in the presence of Raney nickel, of a base, such as sodium hydroxide, potassium hydroxide, lithium hydroxide or ammonium hydroxide, and of a transition metal complex with, for example, iron, cobalt, chromium or tungsten as transition metals, and of a solvent. In this process, the yields of aminocapronitrile are said to be quantitative at conversions of from 45 to 60%. A disadvantage of this process is the working up of the generally toxic transition metal complexes from the reaction mixtures obtained.

It is an object of the present invention to provide an improved process for the preparation of aliphatic alpha, omega-aminonitriles by partial hydrogenation of adiponitrile, which process does not have the abovementioned disadvantages.

We have found that this object is achieved by a process for the preparation of aliphatic alpha,omega-aminonitriles by partial hydrogenation of aliphatic alpha,omega-dinitriles at elevated temperatures and superatmospheric pressure in the presence of a base and of a hydrogenation catalyst, which comprises carrying out the hydrogenation in the presence of ammonia and lithium hydroxide or of a compound which gives lithium hydroxide during the hydrogenation.

Aliphatic alpha,omega-dinitriles of the formula I

   NC—(CH$_2$)$_n$—CN     I where n is an integer from 1 to 10, in particular 2, 3, 4, 5 or 6, are used as starting materials in the novel process. Particularly preferred compounds I are succinonitrile, glutaronitrile, adiponitrile, pimelonitrile and suberonitrile, very particularly preferably adiponitrile.

In the novel process, the dinitriles I described above are partially hydrogenated in the presence of ammonia and lithium hydroxide or of a compound which gives lithium hydroxide under the reaction conditions, using a hydrogenation catalyst, to give alpha,omega-aminonitriles of the formula II

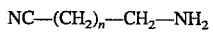   NC—(CH$_2$)$_n$—CH$_2$—NH$_2$     II where n has the abovementioned meanings. Particularly preferred aminonitriles II are those in which n is 2, 3, 4, 5 or 6, in particular 4, i.e. 4-aminobutyronitrile, 5-aminopentanenitrile, 6-aminohexanenitrile (6-aminocapronitrile), 7-aminoheptanenitrile and 8-aminooctanenitrile, very particularly preferably 6-aminocapronitrile.

The reaction is carried out at from 40° to 120° C., preferably from 50° to 100° C., particularly preferably from 60° to 90° C.; the pressure is chosen in general to be from 2 to 12, preferably from 3 to 10, particularly preferably from 4 to 8, MPa. The residence times are essentially dependent on the desired yield and selectivity and on the desired conversion; usually, the residence time is chosen so that a maximum yield is obtained, for example in the range from 50 to 275, preferably from 70 to 200, minutes when adiponitrile is used.

The pressure and temperature ranges are preferably chosen so that the reaction can be carried out in the liquid phase.

Ammonia is used in general in an amount such that the weight ratio of ammonia to dinitrile is from 9:1 to 0.1:1, preferably from 2.3:1 to 0.25:1, particularly preferably from 1.5:1 to 0.4:1.

The amount of lithium hydroxide is chosen as a rule to be from 0.1 to 20, preferably from 1 to 10, % by weight, based on the amount of catalyst used.

Examples of lithium compounds which form lithium hydroxide under the reaction conditions are lithium metal and alkyl- and aryl-lithium compounds, such as n-butyllithium and phenyllithium. The amount of these compounds is chosen in general to give the abovementioned amount of lithium hydroxide.

Preferably used catalysts are nickel-, ruthenium-, rhodium- and cobalt-containing compounds, preferably those of the Raney type, in particular Raney nickel and Raney cobalt. The catalysts may also be used in the form of supported catalysts, suitable carriers being, for example, alumina, silica, zinc oxide, active carbon or titanium dioxide (cf. Appl. Het. Cat. (1987), 106–122; Catalysis, 4 (1981), 1–30). Raney nickel is particularly preferred (for example from BASF AG, Degussa and Grace).

The nickel, ruthenium, rhodium and cobalt catalysts may be modified with metals of group VIB (Cr, Mo, W) and VIII (Fe, Ru, Os, Co (only in the case of nickel), Rh, Ir, Pd, Pt) of the Periodic Table. Observations to date have shown that the use of, in particular, modified Raney nickel catalysts, for example those modified with chromium and/or iron, leads to higher aminonitrile selectivities. (For preparation, cf. DE-A 2 260 978; Bull. Soc. Chem. 13 (1946), 208).

The amount of catalyst is chosen in general so that the amount of cobalt, ruthenium, rhodium or nickel is from 1 to 50, preferably from 5 to 20, % by weight, based on the amount of dinitrile used.

The catalysts may be used in the form of fixed-bed catalysts by the liquid phase or trickle-bed procedure or, preferably, as suspension catalysts.

In the novel process, alpha,omega-aminonitriles are obtained in high yield and in good selectivities. The alpha, omega-aminonitriles are important starting compounds for the preparation of cyclic lactams, in particular 6-aminocapronitrile for caprolactam.

EXAMPLES

Example 1 (Comparative Example similar to WO 92/21650, Example 1)

Reactor: 300 ml autoclave Batch: 60 g of adiponitrile ("ADN"), 7 g of Raney nickel (Ra-Ni) (BASF, H 1–50, water-moist, about 6 g of pure Ra-Ni).

ADN and Ra-Ni were introduced under argon, after which the autoclave was closed and 100 ml of liquid ammonia were added. Thorough mixing was carried out by means of a magnetic stirrer.

After heating to 80° C. (autogenous pressure: about 30 bar), the total pressure was increased to 70 bar by means of hydrogen. The pressure of 70 bar was maintained by continuously introducing further hydrogen. After 30, 60, 90, 120, 180, 240, 300 and 360 minutes, samples were taken and were analyzed by gas chromatography. The test results are shown in Table 1.

TABLE 1

| Time [min] | ACN[1] [%] | HMD[2] [%] | Conversion [%] | ACN selectivity [%] |
|---|---|---|---|---|
| 30 | 45.8 | 6.1 | 52.5 | 87.2 |
| 60 | 61.4 | 12.4 | 74.9 | 82.0 |
| 90 | 63.9 | 23.4 | 89.9 | 71.1 |
| 120 | 57.5 | 34.0 | 95.8 | 60.0 |
| 180 | 31.4 | 61.7 | 100.0 | 31.4 |
| 240 | 17.7 | 74.5 | 100.0 | 17.7 |
| 300 | 7.8 | 83.0 | 100.0 | 7.8 |
| 360 | 2.9 | 86.9 | 100.0 | 2.9 |

[1] ACN = 6-aminocapronitrile; [2] HMD = hexamethylenediamine

Example 2

Reactor: 300 ml autoclave Batch: 60 g of ADN, 7 g of Ra-Ni (BASF, H 1–50, water-moist, about 6 g of Ra-Ni), 0.1 g of LiOH.

ADN, LiOH and Ra-Ni were introduced under argon, after which the autoclave was closed and 100 ml of $NH_3$ were forced in. Thorough mixing was carried out by means of a magnetic stirrer.

After heating to 80° C. (autogenous pressure: about 30 bar), the total pressure was increased to 70 bar by means of hydrogen. The pressure of 70 bar was maintained by continuously introducing further hydrogen. After 30, 60, 90, 120, 180, 240, 300 and 360 minutes, samples were taken and were analyzed by gas chromatography. The test results are shown in Table 2.

TABLE 2

| Time [min] | ACN [%] | HMD [%] | Conversion [%] | ACN selectivity [%] |
|---|---|---|---|---|
| 30 | 14.05 | 0.2 | 14.8 | 98.0 |
| 60 | 40.2 | 1.7 | 42.1 | 95.5 |
| 90 | 54.6 | 3.8 | 58.5 | 93.3 |
| 120 | 65.8 | 7.4 | 73.7 | 89.3 |
| 180 | 73.8 | 18.8 | 93.0 | 79.4 |
| 240 | 62.2 | 36.6 | 99.1 | 62.8 |
| 300 | 43.5 | 56.0 | 100.0 | 43.5 |
| 360 | 26.4 | 73.0 | 100.0 | 26.4 |

Comparison of Examples 1 and 2 demonstrates that, as a result of adding lithium hydroxide, higher aminocapronitrile selectivities are obtained at the same conversion.

Example 3 (Comparative Example using NaOH instead of LiOH)

Example 2 was repeated with 0.2 g of NaOH instead of 0.1 g of LiOH, under otherwise identical test conditions. The results are shown in Table 3.

TABLE 3

| Time [min] | ACN [%] | HMD [%] | Conversion [%] | ACN selectivity [%] |
|---|---|---|---|---|
| 30 | 31.2 | 1.0 | 50.2 | 62.2 |
| 60 | 45.6 | 2.6 | 67.5 | 67.6 |
| 90 | 53.9 | 4.5 | 78.4 | 68.6 |
| 120 | 59.5 | 7.3 | 87.3 | 68.2 |
| 180 | 60.7 | 14.0 | 94.9 | 64.0 |
| 240 | 56.5 | 22.4 | 98.3 | 57.5 |

Comparison of Examples 1, 2 and 3 shows that the addition of NaOH does not result in any increase in the aminocapronitrile selectivity.

We claim:

1. A process for the preparation of aliphatic alpha,omega-aminonitriles of the formula II $$NC-(CH_2)_n-CH_2-NH_2 \quad \text{II}$$

where n is an integer from 1 to 10, by the partial hydrogenation of aliphatic alpha,omega-dinitriles of the formula I $$NC-(CH_2)_n-CN \quad \text{I}$$

where n has the abovementioned meanings, in the presence of a hydrogenation catalyst, ammonia and lithium hydroxide or of a compound which gives lithium hydroxide during the hydrogenation, at a temperature in the range of from 40° to 120° C. and at a pressure in the range of from 2 to 12 MPa, the temperature and pressure being chosen so that the reaction is carried out in the liquid phase, the weight ratio of ammonia to dinitrile I is from 9:1 to 0.1:1, wherein the amount of lithium hydroxide is from 0.1 to 20% by weight, based on the amount of hydrogenation catalyst, wherein the hydrogenation catalyst is a nickel-, ruthenium-, rhodium- or cobalt compound, and wherein the amount of hydrogenation catalyst is chosen so that the amount of nickel, ruthenium, rhodium or cobalt is from 1 to 50% by weight, based on the amount of dinitrile I.

2. The process of claim 1, wherein the hydrogenation catalyst is a Raney nickel catalyst.

3. The process of claim 1, wherein the aliphatic alpha, omega-dinitrile used is adiponitrile, 6-aminocapronitrile being obtained.

* * * * *